United States Patent
Griesbach, III et al.

(10) Patent No.: US 6,663,584 B2
(45) Date of Patent: Dec. 16, 2003

(54) ELASTIC BANDAGE

(75) Inventors: Henry L. Griesbach, III, Clarkston, GA (US); Jae-Ho Kim, Roswell, GA (US); Jeffrey M. Willis, Atlanta, GA (US)

(73) Assignee: Kimberly-Clark Worldwide Inc., Neenah, WI (US)

( * ) Notice: Subject to any disclaimer, the term of this patent is extended or adjusted under 35 U.S.C. 154(b) by 281 days.

(21) Appl. No.: 09/940,220

(22) Filed: Aug. 27, 2001

(65) Prior Publication Data

US 2003/0040691 A1 Feb. 27, 2003

(51) Int. Cl.[7] .................................................. A61F 13/00
(52) U.S. Cl. .............................. 602/75; 602/41; 602/45; 602/76
(58) Field of Search ................................. 602/41–59, 75, 602/76, 77; 428/224, 232, 230, 231, 245, 288, 289, 294, 295, 296, 298

(56) References Cited

U.S. PATENT DOCUMENTS

| | | | |
|---|---|---|---|
| 2,093,910 A | | 9/1937 | Farrell |
| 2,190,378 A | | 2/1940 | Hinkamp et al. |
| 2,560,712 A | | 7/1951 | Bell |
| 3,051,171 A | | 8/1962 | Liloia et al. |
| 3,330,275 A | | 7/1967 | Jenard et al. |
| 3,575,782 A | | 4/1971 | Hansen |
| 3,842,832 A | | 10/1974 | Wideman et al. |
| 3,849,241 A | * | 11/1974 | Butin et al. ............... 161/169 |
| 3,872,862 A | | 3/1975 | Hume |
| 4,005,709 A | | 2/1977 | Laerdal |
| 4,207,885 A | | 6/1980 | Hampton et al. |
| 4,209,563 A | | 6/1980 | Sisson |
| 4,214,582 A | * | 7/1980 | Patel ........................ 128/156 |
| 4,349,020 A | | 9/1982 | Krikorian |

(List continued on next page.)

FOREIGN PATENT DOCUMENTS

| | | |
|---|---|---|
| EP | 0 306 464 B1 | 1/1992 |
| EP | 0 548 609 | 6/1993 |
| EP | 0 651 628 B1 | 9/1997 |
| WO | 89/01345 | 2/1989 |
| WO | 96/28113 | 9/1996 |
| WO | 97/18780 | 5/1997 |
| WO | 98/12996 | 4/1998 |
| WO | 98/57675 | 12/1998 |
| WO | 99/58090 | 11/1999 |
| WO | 00/53139 | 9/2000 |

OTHER PUBLICATIONS

EP 631761 A (Abstract), Date: Jan. 4, 1995; Inventor: R. Demhartner; Assignee: Demhartner GMBH & Co. KGR (Demh–N).

DE 3410169 A (Abstract only), Date: Sep. 26, 1985; Inventor: Jung, H; Langen, G; Schafer, E; Assignee: Braun AG Karl Otto (Brau–N), Braun F. (Brau–I); Braun K O KG (Brau–N); Braun AG KO (Brau–N).

*Primary Examiner*—Kim M. Lewis
(74) *Attorney, Agent, or Firm*—Scott B. Garrison

(57) ABSTRACT

An elastic bandage is disclosed having a nonelastic absorbent nonwoven web, a non-elastic breathable nonwoven web, and a meltspun elastomeric material disposed between the two webs. The meltspun elastomeric material can comprise a plurality of meltspun elastomeric filaments aligned in substantially parallel distribution in a machine direction, the filaments attached to a side of the nonelastic breathable nonwoven web and to a side of the nonelastic absorbent nonwoven web. The nonelastic absorbent nonwoven web can comprise a laminate of nonwoven layers. The nonelastic breathable nonwoven web can comprise a breathable film bonded to a nonwoven layer or laminate individual nonwoven layers. A self adherent coating may be disposed upon an outer surface of the elastic bandage.

27 Claims, 2 Drawing Sheets

U.S. PATENT DOCUMENTS

| | | | |
|---|---|---|---|
| 4,414,970 A | 11/1983 | Berry | |
| 4,552,802 A | 11/1985 | Mechin | |
| 4,609,578 A | 9/1986 | Reed | |
| 4,664,662 A | 5/1987 | Webster | |
| 4,692,368 A | 9/1987 | Taylor et al. | |
| 4,692,371 A | 9/1987 | Morman et al. | |
| 4,699,133 A | 10/1987 | Schafer et al. | |
| 4,707,398 A | 11/1987 | Boggs | |
| 4,720,415 A | 1/1988 | Vander Wielen et al. | |
| 4,724,184 A | 2/1988 | Killian et al. | |
| 4,737,400 A | 4/1988 | Edison et al. | |
| 4,741,949 A | 5/1988 | Morman et al. | |
| 4,756,942 A | 7/1988 | Aichele | |
| 4,789,699 A | 12/1988 | Kieffer et al. | |
| 4,820,293 A | 4/1989 | Kamme | |
| 4,832,010 A | 5/1989 | Lerman | |
| 4,846,164 A | 7/1989 | Martz | |
| 4,863,779 A | 9/1989 | Daponte | |
| 4,879,169 A | 11/1989 | Zafiroglu | |
| 4,909,243 A | 3/1990 | Frank et al. | |
| 4,911,155 A | 3/1990 | Delannoy | |
| 4,926,848 A | 5/1990 | Shimkus et al. | |
| 4,944,958 A | 7/1990 | Langen et al. | |
| 4,957,795 A | 9/1990 | Riedel | |
| 4,977,011 A | 12/1990 | Smith | |
| 4,984,584 A | 1/1991 | Hansen et al. | |
| 5,005,567 A | 4/1991 | Gilman et al. | |
| 5,006,401 A | 4/1991 | Frank | |
| 5,147,338 A | 9/1992 | Lang et al. | |
| 5,156,589 A | 10/1992 | Langen et al. | |
| 5,203,764 A | 4/1993 | Libbey et al. | |
| 5,209,801 A | 5/1993 | Smith | |
| 5,230,701 A | 7/1993 | Meyer et al. | |
| 5,324,252 A | 6/1994 | Libbey et al. | |
| 5,340,363 A | 8/1994 | Fabo | |
| 5,439,438 A | 8/1995 | Ersfeld et al. | |
| 5,445,604 A | 8/1995 | Lang | |
| 5,503,908 A | 4/1996 | Faass | |
| 5,527,270 A | 6/1996 | Chase et al. | |
| 5,593,395 A | 1/1997 | Martz | |
| 5,603,946 A | 2/1997 | Constantine | |
| 5,692,937 A | 12/1997 | Zhang | |
| 5,762,623 A | 6/1998 | Murphy et al. | |
| 5,823,195 A | 10/1998 | Shook et al. | |
| 5,939,339 A | 8/1999 | Delmore et al. | |
| 5,964,973 A | 10/1999 | Heath et al. | |
| 5,973,221 A | 10/1999 | Collyer et al. | |
| 6,011,194 A | 1/2000 | Buglino et al. | |
| 6,040,494 A | 3/2000 | Kalentun et al. | |
| 6,096,668 A | 8/2000 | Abuto et al. | |

* cited by examiner

ELASTIC BANDAGE

BACKGROUND OF THE INVENTION

The present invention relates generally to a wound dressing, and more particularly, to a wound dressing that is a multi-layer, elastic bandage that may be compressively wrapped around a wound and is capable of absorbing fluids and wound exudate while preventing the absorption of external liquids through the bandage. When permeation of moisture vapor is desired, proper selection of the materials can maintain the liquid barrier properties while allowing breathability of moisture vapor.

In the field of medicine, wrappings or bandages have long been used to prevent injury, in addition to providing for protection against re-injury. For example, limbs are wrapped to prevent injury or re-injury to skin, tendons, muscles and/or ligaments as well as to provide support. Similarly, adherent articles, such as bandages or adhesive tapes are commonly used to cover wounds, cuts, blisters, and the like. Such adherent articles typically include an adhesive material that is applied to or used in conjunction with a substrate material. For example, to use an adherent article a portion of the substrate material is positioned over the wound and an adhesive portion either previously conjoined to the substrate or placed over the substrate is adhered to the surrounding skin. The adherence of the substrate material to the skin allows the adherent article to be tightly fitted over the wound to protect the wound from infection.

A widely acceptable form of treatment for chronic leg ulcers is compression therapy. Wrapping products are typically employed so as to apply a pressure of less than about 3 pounds per square inch to the area wrapped. Lower pressures such as, for example, about 1 psi are desirable. In contrast, wraps which exert substantial pressure can cause circulation problems. Further, if the material is folded or creased while being applied, the bandage might provide uneven support or have high tension areas. This ultimately could cause circulation problems in the user's leg. There is often a need to combine compression therapy with the use of an absorbent article. Problems associated with absorbent articles relate to positioning and securing them over a wound bed. Further, when an absorbent article is used, it often must be forcibly torn away from the skin to break the adhesive bond of the substrate with the skin. This frequently results in substantial pain to the user and possible maceration of the wound itself.

DEFINITIONS

The term "elastic" is used herein to mean any material which, upon application of a biasing force, is stretchable, that is, elongatable at least about 60 percent (i.e., to a stretched, biased length which is at least about 160 percent of its relaxed unbiased length), and which, will recover at least 55 percent of its elongation upon release of the stretching, elongating force. A hypothetical example would be a one (1) inch sample of a material which is elongatable to at least 1.60 inches and which, upon being elongated to 1.60 inches and released, will recover to a length of not more than 1.27 inches. Many elastic materials may be elongated by much more than 60 percent (i.e., much more than 160 percent of their relaxed length), for example, elongated 100 percent or more, and many of these will recover to substantially their initial relaxed length, for example, to within 105 percent of their original relaxed length, upon release of the stretching force.

The term "inelastic" or "nonelastic" as used herein refers to any material which does not fall within the definition of "elastic," above.

As used herein the term "extensible" means elongatable or stretchable in at least one direction.

The term "machine direction" as used herein refers to the planar dimension of a nonwoven fibrous web which is in the direction of travel of the forming surface onto which fibers are deposited during formation of the web.

The term "cross-machine direction" as used herein refers to the planar dimension of a nonwoven fibrous web which is in the direction that is perpendicular to the machine direction defined above.

The term "z-direction" as used herein refers to the thickness direction of a sheet of material, that is, the direction perpendicular to the plane of the length and width dimensions.

As used herein, the term "disposable" is not limited to single use articles but also refers to articles that can be discarded if they become soiled or otherwise unusable after only a few uses.

The term "composite elastic material" as used herein refers to an elastic material which may be a multi-component material or a multilayer material. For example, a multilayer material may have at least one elastic layer joined to at least one gatherable layer so that the gatherable layer is gathered between the locations where it is joined to the elastic layer. Such a multilayer composite elastic material may be stretched to the extent that the nonelastic material gathered between the bond locations allows the elastic material to elongate. This type of multilayer composite elastic material is disclosed, for example, by U.S. Pat. No. 4,720,415 to Vander Wielen et al., issued Jan. 19, 1988, and U.S. Pat. No. 6,096,668 to Abuto et al., issued Aug. 1, 2001, and a process for making the same is disclosed, for example, by U.S. Pat. No. 5,964,973 to Heath et al., issued Oct. 12, 1999, all of which are hereby incorporated by reference.

The term "stretch-to-stop" as used herein refers to a ratio determined from the difference between the unextended dimension of a composite elastic material and the maximum extended dimension of a composite elastic material upon the application of a specified tensioning force and dividing that difference by the unextended dimension of the composite elastic material. If the stretch-to-stop is expressed in percent, this ratio is multiplied by 100. For example, a composite elastic material having an unextended length of 5 inches and a maximum extended length of 10 inches upon applying a force of 2000 grams has a stretch-to-stop (at 2000 grams) of 100 percent.

The term "meltspun" as used herein refers to a nonwoven web of filaments or fibers, which are formed by extruding a molten thermoplastic material, or coextruding more than one molten thermoplastic material, as filaments or fibers from a plurality of fine, usually circular, capillaries in a spinneret with the diameter of the extruded filaments or fibers. Meltspun fabrics include, but are not limited to, spunbonded fabrics and meltblown fabrics and are characterized as having thermal bonding junctions throughout the fabric.

As used herein, the terms "nonwoven" and "nonwoven web" mean a web having a structure of individual fibers or threads which are interlaid, but not in an identifiable, repeating manner. Nonwoven webs have been, in the past, formed by a variety of processes such as, for example, meltblowing processes, spunbonding processes and bonded carded web processes.

As used herein, the term "autogenous bonding" means bonding provided by fusion and/or self-adhesion of fibers and/or filaments without an applied external adhesive or bonding agent. Autogenous bonding may be provided by contact between fibers and/or filaments while at least a portion of the fibers and/or filaments are semi-molten or tacky. Autogenous bonding may also be provided by blending a tackifying resin with thermoplastic polymers used to form fibers and/or filaments. Fibers and/or filaments formed from such a blend can be adapted to self-bond with or without the application of pressure and/or heat. Solvents may also be used to cause fusion of fibers and filaments which remains after the solvent is removed.

As used herein, the terms "meltblown", "meltblown fibers", and "meltblown filaments" mean fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, the disclosure of which is hereby incorporated by reference.

As used herein, the term "microfibers" means small diameter fibers having an average diameter not greater than about 100 microns, for example, having an average diameter of from about 0.5 microns to about 50 microns, or more particularly, microfibers may have an average diameter of from about 4 microns to about 40 microns.

As used herein, the terms "spunbond", "spunbonded fibers" or "spunbond filaments" refer to small diameter fibers which are formed by extruding a molten thermoplastic material as filaments from a plurality of fine, usually circular, capillaries of a spinneret with the diameter of the extruded filaments then being rapidly reduced as by, for example, eductive drawing or other well-known spunbonding mechanisms. The production of spun-bonded nonwoven webs is illustrated in patents such as, for example, in U.S. Pat. No. 4,340,563 to Appel et al., and U.S. Pat. No. 3,692,618 to Dorschner et al. The disclosures of these patents are hereby incorporated by reference.

As used herein the terms "substrate", "surface", or "sheet" means a layer that may be a film or woven web or nonwoven web, a laminate; pervious or impervious to air, gas, and/or liquids; or a composite structure comprising for example a topsheet, backsheet, and an absorbent medium therebetween.

As used herein the "layer" when used in the singular can have the dual meaning of a single element or a plurality of elements.

As used herein the term "laminate" includes any multi-layer material where the layers are joined together.

As used herein "SMS laminate" means a spunbond/meltblown/spunbond (SMS) laminate. Examples of multi-layer nonwoven laminates are disclosed in U.S. Pat. No. 4,041,203 to Brock et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate such as by thermal point bonding as described below. Alternatively, the fabric layers may be made individually, collected in rolls, and combined in a separate bonding step.

As used herein the term "palindromic" means a multilayer laminate which is substantially symmetrical. Examples of palindromic laminates would have layer configurations of A/B/A, A/B/B/A, A/A/B/B/A/A, A/B/C/B/A, etc. Examples of non-palindromic layer configurations would include A/B/C, A/B/C/A, A/B/C/D, etc.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" includes all possible special configurations of the molecule. These configurations include, but are not limited to isotactic, syndiotactic and random symmetries.

As used herein the term "amorphous polymer", when used herein to describe a bonding layer either as an intermediate layer or a separately applied layer, means a thermoplastic polymer such as certain polyolefins with a density in the range of from about 0.85 to about 0.89 g/cm.sup.3 and low crystallinity, for example, less than about 30.

As used herein, the term "barrier" means a film, laminate or other fabric which is substantially impermeable to the transmission of liquids and which has a hydrohead of at least 50 mbar water. Hydrohead as used herein refers to a measure of the liquid barrier properties of a fabric. However, it should be noted that barrier fabrics of the present invention can have a hydrohead value greater than 80 mbar, 150 mbar or even 300 mbar water.

As used herein, the term "breathable" refers to a material which is permeable to water vapor having a minimum WVTR of about 300 g/m$^2$/24 hours. The WVTR of a fabric is water vapor transmission rate which, in one aspect, gives an indication of how comfortable a fabric would be to wear. WVTR (water vapor transmission rate) is measured as indicated below and the results are reported in grams/square meter/day. However, often applications of breathable barriers desirably have higher WVTRs and breathable laminates of the present invention can have WVTRs exceeding about 800 g/m m$^2$/day, 1500 g/m$^2$/day, or even exceeding 3000 g/m$^2$/day.

As used herein the term "monolithic" means an unfilled film or film layer.

As used herein, the term "superabsorbent" refers to absorbent materials capable of absorbing at least 10 grams of aqueous liquid (e.g. distilled water per gram of absorbent material while immersed in the liquid for 4 hours and holding substantially all of the absorbed liquid while under a compression force of up to about 1.5 psi.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, particulates and materials added to enhance processability of the composition.

SUMMARY OF THE INVENTION

Thus, a need exists for an inexpensive material which is absorbent, elastic, compressible and suitable for use as a bandage. There is also a need for a bandage having the additional properties of being relatively tough, durable, absorbent, lightweight and permeable to air and water vapor while exhibiting barrier properties against bacterial and liquid entry. For example, a need exists for a self-adhesive wrap or bandage composed substantially or entirely of materials such that the bandage is elastic, compressible, relatively permeable to air and/or water vapor, relatively impermeable to liquid entry, and so inexpensive as to be considered disposable.

Problems associated with previous self-adhesive elastic bandages have been addressed by the multi-layer, absorbent, breathable, compressive elastic bandage of the present invention.

One type of bandage useful in the present invention is referred to as a stretch-bonded laminate. Such a stretch-bonded laminate may be made as generally described, for example, in U.S. Pat. No. 4,720,415 to Vander Wielen et al., U.S. Pat. No. 6,096,668 to Abuto et al., and U.S. Pat. No. 5,964,973 to Heath et al., as well as U.S. Pat. No. 5,503,908 to Faass, issued Apr. 2, 1996 which are hereby incorporated by reference in their entirety.

In one possible embodiment, the elastic bandage may comprise a laminate that is reversibly extensible in at least one direction, desirably along the length of the bandage. For example, the laminate may comprise a plurality of elastomeric nonwoven fibrous strands in combination with at least one nonelastic absorbent nonwoven web. Additionally, the bandage may comprise a breathable liquid barrier layer. This barrier layer may be a film or more desirably a film incorporated as a layer within a second nonelastic nonwoven web. The elastomeric nonwoven fibrous strands may be attached to the first nonelastic nonwoven web and the second nonelastic nonwoven web or the stand alone film under stretched or partially stretched conditions. The elastomeric nonwoven fibrous strands are situated so that they lie between the first nonelastic nonwoven web and the second nonelastic nonwoven web or between the first nonelastic nonwoven web and the film. When the elastomeric nonwoven fibrous strands are attached to the nonelastic nonwoven webs and subsequently allowed to relax, the entire laminate is caused to gather into small folds or wrinkles substantially normal to the length of the elastomeric strands. This arrangement creates a multi-layer bandage having a first and a second surface and a z-direction thickness. The attachment of the elastomeric nonwoven fibrous strands to the nonelastic nonwoven webs can be by thermal point bonding, adhesives, and other means that serve to attach the threads to the webs.

In other embodiments of the present invention, the elastomeric nonwoven fibrous strands or elastomeric filaments may be incorporated into an elastomeric composite web desirably constructed of a nonwoven web of elastomeric fibers which may include meltblown microfibers. In one aspect of the present invention, the elastomeric composite web is a coherent stretchable sheet which can distribute tensioning forces across its width without creating pressure points or areas of concentrated tension. The elastomeric meltblown fibers may be an elastomeric polymer such as, for example, elastomeric polyesters, elastomeric polyurethanes, elastomeric polyamides, elastomeric copolymers of ethylene and at least one vinyl monomer, and elastomeric A-B-A' block copolymers wherein A and A' are the same or different thermoplastic polymer, and wherein B is an elastomeric polymer block or a combination of blocks. The elastomeric polymer may be blended with a processing aid.

In one aspect of the present invention, the elastic composite web may be an anisotropic nonwoven fibrous web containing a substantially homogenous arrangement of meltblown fibers generally aligned along one of the planar dimensions of the web, for example the MD or machine direction. The elastomeric meltblown fibers may also comprise a mixture of elastomeric meltblown fibers and one or more other materials such as, for example, wood pulp, staple-type fibers, particulates or super-absorbent materials. For example, the staple-type fibers may be polyester fibers, polyamide fibers, glass fibers, polyolefin fibers, cellulosic derived fibers, multi-component fibers, natural fibers, absorbent fibers, electrically conductive fibers or blends of two or more of said fibers. The particulate materials may be, for example, activated charcoal, clays, starches, and metal oxides.

In some embodiments, one of the surfaces of the bandage may be self-adherent. In any of the embodiments the barrier layer may comprise a breathable film, non-breathable film, or coating which itself could comprise a separate layer or could be integrated into one of the nonelastic nonwoven webs. The bandage may also be used in combination with a separate dressing or gauze. According to another aspect of the present invention, the elastic component may also comprise an elastomeric web.

In each of the embodiments, a mechanism is desirable to enable the bandage to be applied to a patient in a stretched and secured relation. Examples of such a mechanism include but are not limited to an adhesive self-adherent coating applied to at least one of the surfaces of the bandage, a hook and loop type fastener, an additional wrap, and tape. If an adhesive self-adherent coating or self-adhesive material is used, desirably, the self adhesive material may be applied on at least a portion of at least one exterior surface of the elastomeric composite material so that the peel strength of the self adhesive material is less than the peel strength of the layers of the elastic composite material. In other words, the peel strength of such a material would be less than the peel strength which attaches the elastomeric nonwoven fibrous strands or elastomeric strands to the nonwoven laminate. For example, the peel strength of the self-adhesive material may be at least about 5 percent less than the peel strength which attaches the materials together. As another example, the peel strength of the self-adhesive material may be from about 10 to about 98 percent less than the peel strength which attaches the materials together. As a further example, the peel strength of the self-adhesive material may be from about 20 to about 95 percent less than the peel strength which attaches the materials together. Desirably, the peel strength of the self-adhesive material will be from about 0.1 to about 1.0 pound per inch. For example, the peel strength of the self-adhesive material may be from about 0.3 to about 0.5 pound per inch. Desirably, the amount of force required to unwind a roll of the self-adhesive material will be from about 0.3 to about 2.0 pounds per inch. For example, the amount of force required to unwind a roll of the self-adhesive material may be from about 0.5 to about 1.2 pounds per inch.

The use of a thin film as a barrier layer is advantageous for a number of reasons. A desirable film would be impermeable to liquid water and bacteria and as such would form a very effective shield, which protects a patient from sources of infection external to the skin. The film would also serve to retain body fluids within the body at the site of the wound. The vapor permeability of a breathable film provides a sufficient rate of water vapor transport through the film to allow the skin to breathe normally. In spite of the many advantages of the thin film, some problems exist when it is used alone. As such, desirably the film is used with some form of backing sheet or release sheet since due to its extreme flexibility and limpness, the film may curl over upon itself. Additionally, because of its extreme thinness, the film is fragile and can readily catch on a sharp or rough object resulting in a tearing. Furthermore, the film may stick to itself adding to the difficulty in applying the bandages to a patient. As such it is desirable in any of the embodiments to attach the film to a lightweight nonelastic nonwoven fabric. Desirably the nonwoven fabric could comprise a fabric of about 0.6 osy or less. The combination of a lightweight nonwoven and thin film used in conjunction with the bandage enhances the ability of the bandage to conform to the shape of various parts of the body, even a flexible body part such as a knee or elbow.

Furthermore, according to one aspect of the present invention, the film may comprise a monolithic polyurethane film bonded to a nonelastic nonwoven web, a breathable microporous film, or other suitable breathable liquid barrier. The film may further comprise a polymer and filler wherein microporous voids are located adjacent the filler. The barrier may also comprise a polymer having the inherent ability to transport vapors across the barrier without the presence of a microporous structure.

According to one aspect of the present invention, the coating of self-adhesive material may be located on at least one surface of an outermost layer of the laminate. In some embodiments, the coating of self-adhesive material may be located only on raised portions of gathers formed by the nonelastic material gathering into the small folds or wrinkles created in the material. The coating of self adhesive material may be in the form of a randomly scattered network of hot-melt adhesive filaments and/or fibers. The coating of self-adhesive material may be a coating of any suitable conventional commercially available hot-melt adhesive such as, for example, hot melt adhesives which may be based on blends of polyolefins, adhesive resins, and waxes.

According to the present invention, the nonwoven webs of the present invention may comprise nonwoven webs of fibers such as, for example, webs of spunbonded fibers, webs of meltblown fibers, bonded carded webs of fibers, multi-layer materials including at least one of the webs of spunbonded fibers, meltblown fibers, or a bonded carded web of fibers. One such substrate is designed to be placed proximal to the wound bed. This substrate should be absorbent and may be inherently absorbent or may be treated to create or enhance absorbency by such means as surfactant treatment of a naturally hydrophobic material. Additionally, this substrate may also comprise a nonadherent wound contacting layer so that the bandage does not adhere to the wound bed. Another substrate serves as a protective barrier to prevent the passage of external liquids through the bandage. Desirably the film barrier is attached to or incorporated within this substrate. In some aspects of the present invention, the nonwoven webs form gatherable layers when attached to the elastomeric materials. The substrates may also comprise composite materials composed of a mixture of fibers and one or more other materials such as, for example, wood pulp, staple fibers, particulates or super-absorbent materials. Medicinal materials may be mixed with the fibrous materials.

In yet another aspect of the present invention, the bandage may have a stretch-to-stop elongation of at least about 25 percent. For example, the stretch-to-stop elongation may range from about 35 to about 400 percent or more.

DETAILED DESCRIPTION OF THE INVENTION

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention, which broader aspects are embodied in the exemplary constructions.

Figure 1:
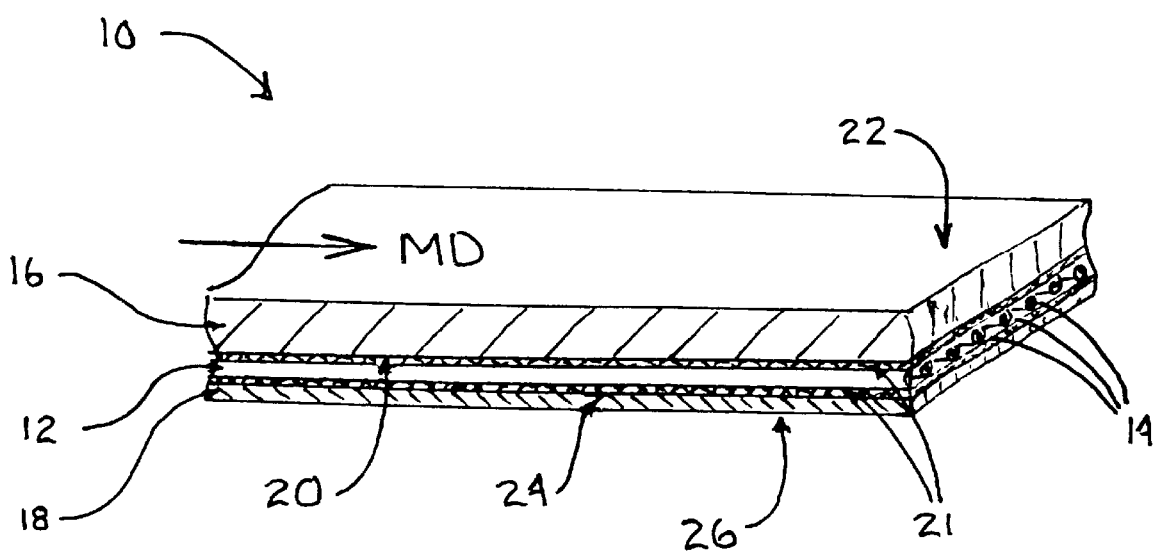
FIG. 1 is a schematic cross-sectional view of an exemplary bandage of the present invention.

Referring now to the drawings wherein like reference numerals represent the same or equivalent structure and, in particular, to FIG. 1 of the drawings there is schematically illustrated an elastic bandage 10 having a meltspun elastomeric material 12 attached to a nonelastic absorbent nonwoven web 16 and a nonelastic breathable web 18. The elastomeric material 12 may comprise a plurality of substantially parallel rows of meltspun elastomeric filaments 14 substantially continuous in length and attached to the webs 16 and 18 so as to be oriented in the machine direction of webs 16 and 18.

The actual number of elastomeric filaments utilized in forming the elastomeric material may be varied depending on the particular characteristics desired in the final product. For example, as few as about 5 separate strands per inch may be used. More desirably, as few as about 10–12 strands per inch may be used. Of course, many more than the 10–12 strands may be used as well and are contemplated in the present invention.

The absorbent nonwoven web 16 has a first side 20 and a second wound contacting side 22. The breathable web 18 also has a first side 24 and a second side 26. The first sides 20 and 24 of the absorbent and breathable webs 16, 18 respectively are attached to the elastomeric material 12. In the case of FIG. 1, the first sides 20 and 24 of the absorbent and breathable webs 16, 18 respectively are attached to the elastomeric filaments 14.

The elastomeric filaments 14 may be attached to the webs 16 and 18 by a number of possible means. Stitching, needle-tacking, ultrasonic welding, thermal bonding, and adhesive bonding are just some of the methods contemplated. In one aspect of the invention, bonding may be achieved either autogenously or through the use of a separate adhesive or as a combination of autogenous and adhesive bonding. Typically, the manufacturing process used to create the elastomeric filaments 14 will have caused them to cool so that by the time they are to be bonded to the webs autogenous bonding alone would not be possible. Therefore, in most embodiments, an adhesive 21, such as a melt-spray type adhesive, is employed. Although, if sufficient tackifying resins, or other adhesive components are utilized either in the facings or in the continuous filaments, then autogenous bonding might be possible.

In certain embodiments, the adhesive is sprayed directly onto the nonwoven sheet material comprising webs 16 and 18. However, other arrangements of adhesive application, such as brushing or the like, may also be utilized. In addition, the adhesive 21 may be applied directly to the sheet material prior to bonding with the elastomeric filaments, may be applied to both the elastomeric filaments and the sheet material prior to bonding, or may be applied to one or both of the filaments and the sheet material while bonding pressure is being applied. The present invention is not limited to any particular bonding mechanism. In certain embodiments, merely applying a spray adhesive to either surface 20 or 24 of webs 16 or 18 respectively, and then contacting this adhesive-carrying facing with the stretched elastomeric filaments 14 and with the second web will result in sufficient bonding strength.

Particular meltspray adhesives that may be utilized include Findley-brand H2525A and Findley-brand H2096, both available from Findley Adhesives (known also as Bostik Findley). These adhesives may be applied through a hot melt spray die at an elevated temperature of approximately 300–375° F. to the first sides 20 and 24 of webs 16 and 18. The meltspray adhesive usually will form a very lightweight layer of about 3 grams per square meter ("gsm") of adhesive in the final composite. These particular Findley adhesives are elastic as well.

In addition, in many particular embodiments of the present invention, the adhesive component is applied to the surface of the nonwoven layer in discreet adhesive lines. The adhesive may be applied in various patterns including random patterns so that the adhesive lines intersect the elastic filament lines to form various types of bonding networks which could include either adhesive-to-elastic bonds or both adhesive-to-elastic bonds and adhesive-to-adhesive bonds. These bonding networks may include a relatively large total number of adhesive-to-elastic and adhesive-to-adhesive bonds that provide the laminated article with increased strength, while utilizing minimal amounts of adhesive. Such enhancements are achieved by the use of lay-down or spray patterns of adhesive formed by spraying adhesive onto the surface of the nonwoven in predetermined arrangements. In most cases, a final product with less adhesive exhibits a reduction in undesirable stiffness, and is generally more flexible and soft than products having more adhesive.

Nip rolls are used to apply pressure to the adhesive-coating facings and the elastomeric filaments to result in the necessary lamination. The webs are bonded together with the elastomeric filaments 14 at fairly high surface pressures, which may be between about 20 and 300 pounds per linear inch ("pli"). A typical bonding pressure may be about 50 pli or about 100 pli. The bonder, or nip roll, (sometimes referred to as "laminator") section of the laminating apparatus (not shown) performs the primary stretching of the elastomeric filaments. The speed ratio of the bonder or nip rolls relative to the chilled rolls can be varied, and in most cases is between about 2:1 and 8:1 and in some is approximately 4:1 to 6:1.

As an alternative, the elastomeric strands 14 may be bonded to a polymeric web (not shown) prior to stretching so that the strands can be handled in a single sheet form. In this embodiment, a tackified meltblown web may be applied onto a set of parallel elastomeric filaments. The web/filament sheet will be stretched and then fed into a calender nip so as to bond facings to the sheet with the use of an adhesive system. When utilized, this particular embodiment allows for occasional filament breakage or imperfection without interrupting the manufacturing process.

The elastomeric material 12 may also comprise an anisotropic nonwoven fibrous web containing a substantially homogenous arrangement of meltblown fibers generally aligned along one of the planar dimensions of the web such as, for example, the machine direction. Such an anisotropic nonwoven fibrous web would be desirable where the elastic component of the self-adhesive composite elastic material does not need the same stretch and recovery properties in every direction. If the elastic component is designed to have the required stretch and recovery properties in only the direction that the nonelastic nonwoven webs 16 and 18 allows the laminate to stretch, then relatively less elastomeric material could be used than if the web was isotropic. Since elastomeric materials generally tend to be quite expensive, reducing the amount of elastomeric material while still achieving the desired physical properties could be accomplished. Such an anisotropic elastic fibrous web may be made as generally described, for example, by U.S. Pat. No. 5,366,793 to Fitts, et al., which is hereby incorporated by reference.

In other aspects of the invention, after bonding of the nonwoven webs 16 and 18 to the elastomeric filaments 14 to form an absorbent nonwoven/meltspun elastomeric filament/breathable nonwoven laminate, the laminate is then allowed to relax and contract to an unstretched or less stretched, condition. The laminate is then wound onto a take-up roll via a surface driven winder. The speed ratio of the winder relative to the bonder rollers results in relaxation of the stretched elastomeric filaments and a retraction of the laminate into a gathered state as the laminate is wound onto the roll. For example, the winder speed to bonder roll speed may be approximately 0 to about 0.75, and may be from about 0.2 to 0.5. The contraction of the elastomeric filaments results in a gathered, stretchable laminate article where the outer facing(s) is gathered between the bonding points.

The overall basis weight of the elastic bandage can vary, but in some applications is between about 65 g/m$^2$ and about 500 g/m$^2$. In other applications, the basis weight may be between about 200 g/m$^2$ and about 500 g/m$^2$. In still other desirable embodiments, the basis weight of the elastic bandage in a stretched state may be between about 200 g/m$^2$ and about 250 g/m$^2$.

Various types of compositions and various processing conditions may be utilized to form the elastomeric filaments 14 themselves. For example, a Kraton®-brand elastic polymer may be fed into an extruder where the polymer is melted at a controlled temperature of between about 260° and 460° F., and in certain instances at about 385° F. In other embodiments, depending on the particular polymer employed, the melt temperature may be approximately 470° F. to 480° F. The polymer is then extruded through a predetermined number of apertures in a spinneret in a generally downward direction into separate continuous filaments by extrusion at a pressure of approximately 300 to 4000 psi (typically from about 1000 to about 2000 psi). Various spinneret capillary configurations may be utilized in the present invention. One particular class of polymers that may be utilized in the present process is the Kraton®) G series of polymers distributed by Shell Chemical Company (now available from Kraton Products U.S.—LLC). Various Kraton® polymers may be utilized such as Kraton®2760 and Kraton®6631.

However, the present invention is not limited to this or any particular polymer or material from which to form the elastomeric filaments. For example, various materials, including the following, may be used: polypropylene and its copolymers, polyethylene and its copolymers, polyesters, polyethylene terephthalate, polybutane, polymethyldentene, ethylenepropylene co-polymers, polyamides, tetrablock polymers, styrenic block copolymers, polyhexamethylene adipamide, poly-(oc-caproamide), polyhexamethylenesebacamide, polyvinyls, polystyrene, polyurethanes, thermoplastic polymers, polytrifluorochloroethylene, ethylene vinyl acetate polymers, polyetheresters, polyurethane, polyurethane elastomerics, polyamide elastomerics, polyamides, viscoelastic hot melt pressure sensitive adhesives. In addition, such materials may be utilized to extrude singleconstituent, bi-constituent, and bi-component filaments within the scope of the presently described invention. The elastomeric fibers may also be a mixture of elastomeric meltblown fibers and one or more other materials such as, for example, wood pulp, staple-type fibers, particulates or super-absorbent materials. For example, the staple-type fibers may be polyester fibers, polyamide fibers, glass fibers, polyolefin fibers, cellulosic derived fibers, multi-component fibers, natural fibers, absorbent fibers, electrically conductive fibers or blends of two or more of said fibers. The particulate materials may be, for example, activated charcoal, clays, starches, and metal oxides.

Other exemplary elastomeric materials that may be used include polyurethane elastomeric materials such as those available under the trademark ESTANE from B. F. Goodrich & Co., polyamide elastomeric materials such as those available under the trademark PEBAX from the Rilsan Company, and polyester elastomeric materials such as those available under trade designation HYTREL from E. I. DuPont De Nemours & Company. However, the invention is not limited to only such elastomeric materials. For example, various latent elastic materials such as the Arnitel-brand polymers may be utilized to provide the necessary elasticity characteristics to the elastomeric filaments.

Generally speaking, the absorbent nonwoven web 16 and the breathable nonwoven web 18 comprise, for example, a web of spunbonded fibers, a web of meltblown fibers, a bonded carded web of fibers, a multi-layer material including at least one of the webs of spunbonded fibers, meltblown fibers, or bonded carded web of fibers. Any suitable non-elastomeric fiber forming resins or blends containing the same may be utilized to form the nonwoven gatherable layer of material. For example, such polymers include polyolefins, non-elastomeric polyesters, non-elastomeric polyamides, cellulosic derived polymers, vinyl chlorides and polyvinyl alcohols.

The nonwoven portions of webs 16 and 18 can be a composite material composed of a mixture of meltblown fibers and other fibrous materials and/or particulates. For an example of such a mixture, reference is made to U.S. Pat. No. 4,100,324 to Anderson et al., incorporated herein by reference, in which meltblown fibers and other fibrous materials are commingled to form a single coherent web of randomly dispersed fibers. Another example of such a composite web would be one made by a technique such as disclosed in U.S. Pat. No. 4,741,949 to Morman et al., also incorporated herein by reference. That patent discloses a nonwoven material which includes a mixture of meltblown thermoplastic fibers and other materials. The fibers and other materials are combined in the gas stream in which the meltblown fibers are borne so that an intimate entangled commingling of meltblown fibers and other materials, e.g., wood pulp, staple fibers or particulates such as, for example, activated charcoal, clays, starches, or hydrocolloid (hydrogel) particulates commonly referred to as super-absorbents occurs prior to collection of the fibers upon a collecting device to form a coherent web of randomly dispersed fibers.

The absorbent nonwoven web 16 is used to absorb and hold fluid exuded by wounds until its reaches its saturated capacity. Such layers can consist of inherently absorbent fibers, such as described in U.S. Pat. No. 3,709,221 to Riely or hydrophilic meltspun filaments and fibers, and laminates thereof as described in U.S. Pat. No. 5,901,706 to Griesbach et al., and U.S. Pat. No. 5,540,979 to Yahiaoui et al. Web 16 can also comprise layered absorbents such as those described in U.S. Pat. No. 4,798,603 to Meyer et al. and U.S. Pat. No. 5,364,382 to Latimer et al. Since the second side or wound contacting side 22 otherwise known as the inner face of the absorbent nonwoven 16 is intended to contact the wound area, it is desirable that the inner face 22 comprise a macroporous fibrous layer to obtain increased strength, greatest porosity, and nonadherency to the wound. The porosity must be great enough to allow body fluids to pass through the pores with insufficient pressure drop, despite the non-wetted characteristic, and small enough to prevent fibers of the absorbent layer from extending through to contact the wound.

It is important that the inner face 22 which is intended to rest against the wound area be nonadherent to the wound surface, otherwise, fibers might be left behind on the wound, causing possible future complications, and the dressing might tend to pull open a partially healed wound, when being pulled off. To avoid this problem, the fibers on the skin- or wound-contacting face are formed of, or coated or impregnated with, a material which is not wetted by body fluids, so that when the body fluids dry, they do not form an adherent bond to that face of the layer. The macroporous, non-wetted, physiologically inert inner face 22 is desirably formed of a spunbond. Other materials can be used, including nets, apertured films, thermally bonded carded webs, and woven scrims. The inner fabric can be treated with a nonadherent, physiologically inert, liquid-repellent polymer such as fluorocarbon, including the chlorofluorocarbon, polymers or silicone polymers. The nonadherent layer also separates the absorbed liquid in the absorbent layer from the wound surface. The liquid absorbed by the absorbent layer is thus separated from the wound area by the non-wetted inner fabric layer. The absorbent nonwoven web 16 can itself comprise spunbond or it can comprise a laminate containing layers of meltblown fibers, spunbond fibers, bonded carded webs and the like. The layers can be palindromic such as an SMS laminate but can be non-palindromic as well.

The breathable nonwoven web 18 is used to prevent external sources of liquid from migrating through the bandage to the wound bed while allowing vapor transmission from the wound through the bandage. In one aspect of the invention, the breathability and liquid barrier properties are obtained by the use of a breathable film. The use of a thin film is advantageous for a number of reasons. The film is impermeable to liquid water and to bacteria and as such forms a very effective shield which protects a patient from sources of infection external to the skin. The film also retains body fluids within the body at the site of the wound. The vapor permeability of the film provides a sufficient rate of water vapor transport through the film to allow the skin to breathe normally. The film may comprise a monolithic film such as polyurethane, a breathable microporous film, or some other suitable breathable liquid barrier. The film may further comprise a polymer and filler wherein microporous voids are located adjacent the filler. The barrier may also comprise a polymer having the inherent ability to transport across the barrier without the presence of a microporous structure.

Figure 2:
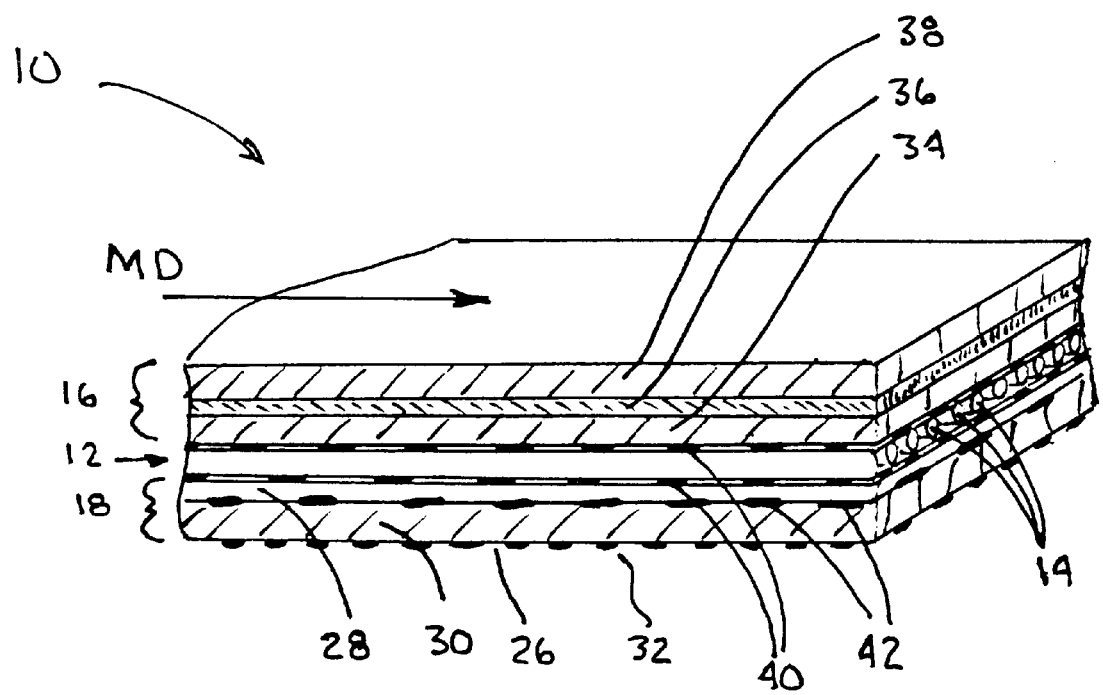
FIG. 2 is a schematic cross-sectional view of another exemplary embodiment of the bandage of the present invention.

In some desirable embodiments such as depicted at FIG. 2, a breathable film 28 is attached to a lightweight nonwoven fabric 30 of 0.6 osy or less, the combination forming the breathable web 18. The film 28 may be attached to the nonwoven fabric 30 by thermal bonding 42. Additional nonwoven layers may be used as well. Desirably the film is not situated on an exterior surface of the bandage, but is protected by at least one outer layer of nonwoven material. FIG. 2 also depicts the alternative embodiment in which the absorbent nonwoven web 16 comprises a laminate. In this case web 16 comprises a spunbond layer 34, a meltblown layer 36 and a spunbond layer 38. The nonwoven webs 16 and 18 are bonded to the meltspun elastomeric material 12 via spaced apart bond points 40.

The combination of lightweight nonwovens and thin films in conjunction with the other elements of the invention provides an elastic bandage having the desired properties specified above as well as the ability to conform to the shape of various parts of the body, even a flexible body part such as a knee or elbow.

In some aspects of the invention, a coating of a self-adhesive material 32 is added to the second surface 26 of at least a portion of the breathable nonwoven web 18 so that the bandage is caused to adhere to itself. The peel strength of the self-adhesive material is less than the peel strength of the layers which attach the elastomeric material to the breathable and absorbent webs. It is very desirable that the peel strength of the self-adhesive material be less than the peel strength which binds the elastic composite material to prevent delamination (i.e., separation of the layers) of the bandage.

For example, the peel strength of the self-adhesive material may be at least about 5 percent less than the peel strength which binds the elastic composite material. As another example, the peel strength of the self-adhesive material may be from about 10 to about 98 percent less than the peel strength which binds the elastic composite material. As a further example, the peel strength of the self-adhesive material may be from about 20 to about 95 percent less than the peel strength which binds the elastic composite material. Desirably, the peel strength of the self-adhesive material will be from about 0.1 to about 1.0 pound per inch. For example, the peel strength of the self-adhesive material may be from about 0.3 to about 0.5 pound per inch. Desirably, the amount of force required to unwind a roll of the self-adhesive material will be from about 0.3 to about 2.0 pounds per inch. For example, the amount of force required to unwind a roll of the self-adhesive material may be from about 0.5 to about 1.2 pounds per inch.

While it is contemplated that the self-adhesive material may be an organic solvent based adhesive or water based adhesive (e.g., latex adhesive) that can be printed, brushed or sprayed onto the elastic composite material, it is desirable that the coating of self adhesive material be in the form of a randomly scattered network of hot-melt adhesive filaments and/or fibers produced by conventional hot-melt adhesive spray equipment. The coating of hot-melt self-adhesive material may also desirably be applied in patterns such as, for example, semi-cycloidal patterns. For example, a self-adhesive material such as a hot-melt self adhesive material may be applied to a composite elastic material as generally described by U.S. Pat. No. 4,949,668 to Heindel, et al., which is hereby incorporated by reference. Desirably, the hot-melt adhesive coating should be applied while the stretch-bonded laminate material is under a relatively small amount of tension. For example, the hot-melt adhesive coating can be applied while the stretch-bonded laminate material is under only enough tension needed to have the material travel through the adhesive application process.

The coating of self-adhesive material may be a coating of any suitable conventional commercially available hot-melt adhesive such as, for example, hot melt adhesives which may contain a blend of thermoplastic polymers (e.g., thermoplastic polyolefins), adhesive resins, and waxes.

Exemplary hot-melt self-adhesive materials which may be used include auto-adhesive 6631-117-1 and auto-adhesive 6631-114-4 available from the National Starch & Chemical Company, Adhesives Division, Bridgewater, N.J. Other self-adhesive materials may be, for example, Hot Melt Adhesive H-9140 available from Findley Adhesives, Incorporated, Wauwatosa, Wis. These self-adhesive materials may be blended with other materials such as, for example antioxidants, stabilizers, surfactants, flow promoters, particulates and materials added to enhance processability of the composition.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An elastic bandage comprising:
  a meltspun elastomeric material;
  a nonelastic absorbent nonwoven web attached to a first side of the elastomeric material; and
  a non-elastic breathable web attached to a second side of the elastomeric material;
  wherein the breathable web is a laminate comprising a nonwoven web and a breathable film.

2. The elastic bandage of claim 1 wherein the meltspun elastomeric material further comprises a plurality of meltspun elastomeric filaments aligned in substantially parallel distribution along the machine direction and are adhesively attached to both the absorbent nonwoven web and the breathable web.

3. The elastic bandage of claim 1 wherein the meltspun elastomeric material further comprises a meltspun elastomeric web.

4. The elastic bandage of claim 1 wherein the breathable film and nonwoven web are adhesively attached to one another in substantially overlapping relation.

5. The elastic bandage of claim 1 wherein the breathable film and nonwoven web are attached to one another at spaced apart bond points.

6. The elastic bandage of claim 5 wherein the breathable film and nonwoven web are attached to one another via thermal bonds.

7. The elastic bandage of claim 1 wherein the breathable film is a microporous film.

8. The elastic bandage of claim 1 wherein the breathable film is a monolithic film.

9. The elastic bandage of claim 8 wherein the breathable film comprises polyurethane.

10. The elastic bandage of claim 1 wherein the bandage is self adherent.

11. The elastic bandage of claim 10 wherein the self-adherent coating is in the form of a randomly scattered network of hot melt adhesive filaments and fibers.

12. The elastic bandage of claim 1 wherein the absorbent nonwoven web is non-adherent.

13. The elastic bandage of claim 1 wherein the absorbent nonwoven web comprises a spunbond layer.

14. The elastic bandage of claim 1 wherein the absorbent nonwoven web comprises a carded web.

15. An elastic bandage comprising:

a nonelastic absorbent nonwoven web;

a plurality of meltspun elastomeric filaments adhesively attached to a first side of the nonwoven web;

a non-elastic breathable web adhesively attached to a second side of the meltspun elastomeric filaments such that the meltspun elastomeric filaments are disposed between the nonwoven web and the breathable web; and a self adherent coating disposed upon one surface of the breathable web;

wherein the breathable web is a laminate comprising a nonwoven web and a breathable film.

16. The elastic bandage of claim 15 wherein the breathable film comprises a microporous film adhesively attached to the nonwoven web in substantially continuous adjacent relation.

17. The elastic bandage of claim 15 wherein the absorbent nonwoven web comprises a non-adherent spunbond layer.

18. The elastic bandage of claim 15 wherein the self-adherent coating is in the form of a randomly scattered network of hot melt adhesive filaments and fibers.

19. The elastic bandage of claim 15 wherein the meltspun elastomeric filaments are aligned in substantially parallel distribution along the machine direction and are adhesively attached to both the absorbent nonwoven web and the breathable web.

20. An elastic bandage comprising:

a nonelastic absorbent non-adherent nonwoven web;

a non-elastic breathable laminate of a nonwoven web and a breathable film;

a plurality of meltspun elastomeric filaments aligned in substantially parallel distribution along the machine direction and further adhesively attached to a first side of the nonwoven web and a first side of the breathable laminate such that the elastomeric filaments are disposed between the nonwoven web and the breathable laminate; and a self adherent coating disposed upon a second surface of the breathable laminate.

21. An elastic bandage comprising:

a nonelastic absorbent non-adherent nonwoven web having a first and a second side;

a non-elastic breathable web having a first and a second side;

a breathable film attached to the first side of the non-elastic breathable web;

a plurality of meltspun elastomeric filaments aligned in substantially parallel distribution in a machine direction, the filaments attached to a first side of the nonwoven web and to the breathable film such that the filaments are disposed between the nonwoven web and the breathable film; and a self adherent coating disposed upon the second surface of the breathable web.

22. The elastic bandage of claim 21 wherein the breathable film is a microporous film.

23. The elastic bandage of claim 21 wherein the breathable film is a monolithic film.

24. The elastic bandage of claim 23 wherein the breathable film comprises polyurethane.

25. The elastic bandage of claim 21 wherein the nonwovens comprise a combination of spunbond and meltblown layers.

26. The elastic bandage of claim 21 wherein the absorbent nonwoven web comprises a carded web.

27. The elastic bandage of claim 21 wherein the self-adherent coating is in the form of a randomly scattered network of hot melt adhesive filaments and fibers.

* * * * *